United States Patent [19]

Lucas

[11] Patent Number: 5,336,661
[45] Date of Patent: Aug. 9, 1994

[54] METHOD FOR ENHANCING TURF QUALITY OF BENT GRASS

[75] Inventor: Leon T. Lucas, Raleigh, N.C.

[73] Assignee: North Carolina State University, Raleigh, N.C.

[21] Appl. No.: 3,632

[22] Filed: Jan. 13, 1993

[51] Int. Cl.$^5$ .................... A01N 47/14; A01N 57/12; A01N 59/06

[52] U.S. Cl. .................... 504/126; 504/143; 514/141; 514/491

[58] Field of Search .............. 514/141, 491; 504/126, 504/127, 143, 190, 194, 301

[56] References Cited

U.S. PATENT DOCUMENTS

| 4,139,616 | 2/1979 | Ducret et al. | 424/222 |
| 4,698,334 | 10/1987 | Horriere et al. | 514/141 |
| 4,806,445 | 2/1989 | Horriere et al. | 514/141 |

OTHER PUBLICATIONS

*FORE* Speciment Label, Apr. (1985).
*CHIPCO*, Speciment Label, (1992).

Primary Examiner—Glennon H. Hollrah
Assistant Examiner—Brian G. Bembenick
Attorney, Agent, or Firm—Bell, Seltzer, Park & Gibson

[57] ABSTRACT

Fungicidal compositions for the protection of turfgrass against crown and root rot are disclosed. The compositions comprise, as the active material, a mixture of (a) a monoester salt of a phosphorous acid (preferably aluminum ethyl phosphite), and (b) an ethylene bisdithiocarbamate contact fungicide (preferably manganese-zinc ethylene bisdithiocarbamate). Preferred compositions comprise one part by weight of the monoester salt to two parts by weight of the ethylene bisdithiocarbamate.

3 Claims, No Drawings

METHOD FOR ENHANCING TURF QUALITY OF BENT GRASS

FIELD OF THE INVENTION

The present invention concerns methods and compositions for the control of crown and root rot in turfgrass with synergistic combinations of alkyl phosphite fungicides and metallic ethylene bisdithiocarbamate fungicides.

BACKGROUND OF THE INVENTION

Crown and root rot is a serious disease of turfgrasses, especially highly maintained turfgrasses as found in lawns, golf courses, nursery crops, and other landscape architecture applications. Current techniques for controlling this disease are not entirely satisfactory, and there is a continuing need for new treatments thereof.

U.S. Pat. No. 4,698,334 to Horriere et al. and U.S. Pat. No. 4,806,445 to Horriere et al. propose fungicidal compositions based on alkyl phosphites in combination with various contact fungicides such as Mancozeb. U.S. Pat. No. 4,139,616 to Ducret et al. describes fungicidal compositions based on alkyl phosphites. None of these concern the treatment of turfgrasses.

SUMMARY OF THE INVENTION

Fungicidal compositions for the protection of turfgrass against crown and root rot are disclosed. The compositions comprise as the active material a synergistic mixture of:

(a) a monoester salt of a phosphorous acid of formula (I):

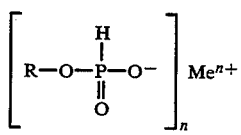

in which

R is an alkyl radical having 2 to 4 carbon atoms,

Me is an alkali metal, alkaline earth, or aluminum atom, and n is a whole number from 1 to 3 equal to the valence of Me; and (b) a metallic ethylene bisdithiocarbamate contact fungicide.

Also disclosed is a process for treating turfgrass to protect the turfgrass from crown and root rot. The process comprises applying to the turfgrass, in a synergistic combination amount effective to control the crown and root rot:

(a) a monoester salt of a phosphorous acid of formula (I) as given above; and (b) a metallic ethylene bisdithiocarbamate contact fungicide. The two active agents may be applied separately, or may be applied together, such as by applying a composition as given above.

The foregoing and other objects and aspects of the present invention are described in detail below.

DETAILED DESCRIPTION OF THE INVENTION

The methods and compositions described herein are useful for treating crown and root rot in turfgrass. Crown and root rot, which causes a decline in turfgrass quality during hot, wet weather, is a disease complex apparently caused by *Pythium* species and *Rhizoctonia* species in combination with environmental stress.

Monoester salts of phosphorus acids useful for carrying out the present invention, as given in formula (I) above, are known. See, e.g., U.S. Pat. No. 4,139,616 to Ducret et al., U.S. Pat. No. 4,698,334 to Horriere et al., and U.S. Pat. No. 4,806,445 to Horriere et al. (the disclosures of all U.S. patents cited herein are to be incorporated herein by reference). Examples include calcium ethyl phosphite, sodium ethyl phosphite, aluminum ethyl phosphite, magnesium isopropyl phosphite, calcium isopropyl phosphite, aluminum isopropyl phosphite, magnesium ethyl phosphite, magnesium isobutyl phosphite, magnesium sec-butyl phosphite, calcium isobutyl phosphite, aluminum N-butyl phosphite, aluminum sec-butyl phosphite, and aluminum isobutyl phosphite. Most preferred is aluminum ethyl phosphite (also called aluminum tris (O-ethyl phosphonate)).

Metallic ethylene bisdithiocarbamate contact fungicides, such as maneb (manganese ethylene bisdithiocarbamate) and mancozeb (manganese-zinc ethylene bisdithiocarbamate), are known. See, e.g., U.S. Pat. No. 4,698,334 to Horriere et al., and U.S. Pat. No. 4,806,445 to Horriere et al. Mancozeb is currently preferred.

Synergistic combinations of the foregoing two active ingredients (the two together being referred to herein as the "active material") are, in general, one part by weight of the compound of formula (I) above in combination with from 1.5 to 2.5 parts by weight of the metallic ethylene bisdithiocarbamate, or more preferably one part by weight of the compound of formula (I) above in combination with from 1.75 to 2.25 parts by weight of the metallic ethylene bisdithiocarbamate. A preferred combination is one part by weight of the compound of formula (I) above in combination with from two parts by weight of the metallic ethylene bisdithiocarbamate.

The synergistic combinations according to the invention may be used with advantage in admixture with one another or with other known fungicides, such as basic salts or hydroxides of copper (oxychloride, oxysulphate), (tetrahydro)phthalimides (captan, captafol, folpel), N-(1-butyl carbamoyl)-2--benzimidazole, methyl carbamate (benomyl), 1,2-di-(3-methoxy or ethoxy)carbonyl-2-thioureido benzenes (thiophanates), methyl 2-benzimidazole carbamate, etc., either to complete the range of activity of the compounds according to the invention or to increase their persistence.

The synergistic combinations according to the invention may also be mixed with other fungicidal, anti-mildew phosphorus derivatives, especially 2-hydroxy-1,3,2-dioxaphospholanes, β-hydroxy ethyl phosphites and phosphorous acid and its salts.

For their practical application, the active ingredients in the synergistic combinations are used as part of a formulated product which, as a rule, contains a support and/or a surfactant in addition to the active material according to the invention.

In the context of the invention, a support is an organic or mineral, natural or synthetic material with which the active material is associated to facilitate its application to the plant, to seeds or to soil, or its transportation or handling. The support can be solid (clays, natural or synthetic silicates, resins, waxes, solid fertilizers) or fluid (water, alcohols, ketones, petroleum fractions, chlorinated hydrocarbons, liquefied gases).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, soluble powders, dusting powders, granulates, solutions, emulsifiable concentrates, emulsions, suspended concentrates and aerosols.

The wettable powders according to the invention can be prepared in such a way that they contain from 20 to 95% by weight of the active material, and they normally contain, in addition to a solid support, from 0 to 5% by weight of a wetting agent, from 3 to 10% by weight of a dispersant and, when necessary, from 0 to 10% by weight of one or more stabilizers and/or other additives, such as penetration agents, adhesives or antilumping agents, colorants, etc.

One example of the compositions of a wettable powder is given in Table 1 below:

TABLE 1

| | |
|---|---|
| active material | 80% |
| calcium lignosulphate (deflocculant) | 5% |
| anionic wetting agent | 1% |
| antilumping silica | 5% |
| kaolin (filler) | 9% |

Powders soluble in water are obtained by mixing from 20 to 95% by weight of the active material, from 0 to 10% of an antilumping agent, the remainder being a hydrosoluble filler mainly a salt.

An example of a composition of the present invention as a soluble powder is given in Table 2 below:

TABLE 2

| | |
|---|---|
| active material | 70% |
| anionic wetting agent | 0.5% |
| antilumping silica | 5% |
| sodium sulfate (soluble filler) | 24.5% |

Aqueous dispersions and emulsions, for example compositions obtained by diluting with water a wettable powder or an emulsifiable concentrate according to the invention, are included within the general scope of the invention. These emulsions can be of the water-in-oil type or of the oil-in-water type, and can have a thick consistency resembling that of a "mayonnaise".

The compositions according to the invention can contain other ingredients, for example protective colloids, adhesives or thickeners, thixotropic agents, stabilizers or sequestrants, as well as other active materials known to have pesticidal properties, especially acaricides or insecticides.

The present invention can be practiced with all turfgrasses, including cool season turfgrasses and warm season turfgrasses. Examples of cool season turfgrasses are Bluegrasses (*Poa* L.), such as Kentucky Bluegrass (*Poa pratensis* L.), Rough Bluegrass (*Poa trivialis* L.), Canada Bluegrass (*Poa compressa* L.), Annual Bluegrass (*Poa annua* L.), Upland Bluegrass (*Poa glaucantha* Gaudin), Wood Bluegrass (*Poa nemoralis* L.), and Bulbous Bluegrass (*Poa bulbosa* L.); the Bentgrasses and Redtop (*Agrostis* L.), such as Creeping Bentgrass (*Agrostis palustris* Huds.), Colonial Bentgrass (*Agrostis tenius* Sibth.), Velvet Bentgrass (*Agrostis canina* L.), South German Mixed Bentgrass (*Agrostis* L.), and Redtop (*Agrostis alba* L.); the Fescues (*Festuca* L.), such as Red Fescue (*Festuca rubra* L.), Chewings Fescue (*Festuca rubra* var. *commutata* Gaud.), Sheep Fescue (*Festuca ovina* L.), Hard Fescue (*Festuca ovina* var. *duriuscula* L. Koch), Hair Fescue (*Festuca capillata* Lam.), Tall Fescue (*Festuca arundinacea* Schreb.), Meadow Fescue (*Festuca elatior* L.); the Ryegrasses (*Lolium* L.), such as Perennial Ryegrass (*Lolium perenne* L.), Italian Ryegrass (*Lolium multiflorum* Lam.); the Wheatgrasses (*Agropyron* Gaertn.), such as Fairway Wheatgrass (*Agropyron cristatum* (L.) Gaertn.), Western Wheatgrass (*Agropyron smithii* Rydb.). Other cool season turfgrasses include Beachgrass (*Ammopnila* Host.), Smooth Brome (*Bromus inermis* Leyss.), Timothy (*Phleum* L.), Orchardgrass (*Dactylis glomerata* L.), Crested Dog's-Tail (*Cynosurus cristatus* L.). Examples of warm season turfgrasses are the Bermudagrasses (*Cynodon* L. C. Rich), such as the Zoysiagrasses (*Zoysia* Willd.), St. Augustinegrass (*Stenotaphrum secundatum* (Walt.) Kuntze), Centipedegrass (*Eremochioa ophiuroides* (Munro.) Hack.), Carpetgrass (*Axonopus* Beauv.), Bahiagrass (*Paspalum notatum* Flugge.), Kikuyugrass (*Pennisetum clandestinum* Hochst. ex Chiov.), Buffalograss (*Buchloe dactyloides* (Nutt.) Engelm.), Blue Grama (*Bouteloua gracilis* (H.B.K.) Lag. ex Steud.), Sideoats Grama (*Bouteloua curtipendula* (Michx.) Torr.), and Dichondra (*Dichondra* Forst.). Cool season turfgrasses are preferred. More preferred is Bluegrass, Bentgrass and Redtop, Fescue, and Ryegrass. Bentgrass is most preferred.

The active materials are, in general, applied to turfgrass either together or separately by spraying a liquid formulation (e.g., an aqueous formulation, including emulsions, or an oil-based formulation) thereof on the turfgrass. The ethylene bisdithiocarbamate contact fungicide is typically applied in an amount of from 10 to 25 pounds per acre (about 10 to 25 Kilograms per Hectare), more preferably in an amount of from 15 to 20 pounds per acre (about 15 15 to 20 Kg per hectare), and still more preferably in an amount of from 17 to 18 pounds per acre (about 17 to 18 Kg per Hectare). The compound of Formula (I) is, in general, applied in an amount of from 2/5 to ⅔, or more preferably ½, times the amount of the compound of Formula (I) (e.g., from about 5 to 17 pounds per acre).

The present invention is explained in greater detail in the following non-limiting examples.

EXAMPLE 1–8

These examples were carried out to identify fungicide and combinations thereof which would have activity against crown and root rot. Fungicides were evaluated on a one-year-old stand of the bentgrass cultivar "Pencross" planted in Raleigh, N.C. U.S.A. The bentgrass was planted in native soil and maintained under conditions similar to a golf green with a mowing height of 0.635 cm (0.25 inches). The fungicides which have activity against *Pythium* species include KOBAN TM (active ingredient: etridiazole) obtained from Grace-Sierra, ALIETTE TM (active ingredient: fosetyl-Al) obtained from Rhone-Poulenc, and SUBDUE TM (active ingredient: metalaxyl) obtained from Ciba-Geigy. The fungicide which has activity against *Pythium* and *Rhizoctonia* species is FORE TM (active ingredient: mancozeb) obtained from Rhom and Hass.

The fungicides were applied separately and in combination at labelled rates to 1.5 m × 1.5 m (5 ft × 5 ft) plots of bentgrass prior to evidence of any decline in turf quality due to root and crown rot. A $CO_2$ backpack sprayer was used to apply the fungicide treatments at (30 lbs psi) using TEEJET TM 8004 nozzles to apply 9.5 liters (2.5 gallons) of fungicide dilutions per 93 square meters (1000 sq ft). The fungicides were initially applied on June 16 and subsequently reapplied 4 times on June 29, July 14, July 29, and August 14, according to a 14 day schedule.

Turf quality, color and percent disease ratings were recorded weekly, based on a scale from 1–10, with 10 being ideal turf quality and color and 1 being all turf dead. The percent disease ratings were calculated based on the percent of area in each plot showing symptoms of brown patch. Turf quality and color ratings were used as an indicator of the health of the bentgrass and the amount of decline associated with root and crown rot. *Pythium* and *Rhizoctonia* species of fungi were isolated from the bentgrass in the experiment during the test period.

Table 3 below indicates that the Fosetyl-Al plus Mancozeb treatment (7.8) yielded a significant improvement in turf color over the check (6.3) and all other treatments within weeks of the first application. Turf quality and color were significantly better on July 7 in the Fosetyl-Al plus Mancozeb treatment (7.8 and 8.0, respectively) than in the check (5.0 and 5.3, respectively) and much better than the Mancozeb (6.8 and 6.8, respectively) and Fosetyl-Al (6.0 and 6.0, respectively) alone. This trend continued throughout the study with the turf quality and color ratings being much better for the Fosetyl-Al plus Mancozeb treatment on August 3 (8.0 and 8.8, respectively) than for the check (4.0 and 4.5, respectively), for Fosetyl-Al alone (5.5 and 5.5, respectively), or for Mancozeb alone (5.5 and 6.5, respectively)- Percent brown patch was much lower in the Fosetyl-Al plus Mancozeb treatment (0) than in the check (37.5), the Mancozeb alone (13.8) or the Fosetyl-Al alone (21.3). Furthermore, surface temperature, which is an indicator of heat stress on bentgrass, was significantly lower on August 3 in the Fosetyl-Al plus Mancozeb treatment (98.1) than in the check (102.8) and all other treatments.

TABLE 3

Evaluation of Fungicides Against Crown and Root Rot

| Treatment # | Pesticide Name | Formula | LBai/A | Turf Quality 6/29 | Turf Color 6/29 | Turf Quality 7/7 | Turf Color 7/7 | % Brown Patch 7/7 | Turf Quality 7/10 | Turf Color 7/10 | Turf Quality 7/21 | Turf Color 7/21 | % Brown Patch 7/22 |
|---|---|---|---|---|---|---|---|---|---|---|---|---|---|
| 1 | Check | — | — | 6.3 | 6.3 | 5.0 | 5.3 | 2.5 | 5.0 | 5.3 | 5.0 | 5.5 | 37.5 |
| 2 | Etridiazole | WP 30 | 2.45 | 6.5 | 6.3 | 5.3 | 5.0 | 2.5 | 5.0 | 5.0 | 5.3 | 5.8 | 28.8 |
| 3 | Etridiazole Metalaxyl | WP 30 EC 2 | 2.45 1.36 | 5.8 | 6.0 | 4.5 | 4.8 | 3.8 | 4.3 | 4.8 | 5.5 | 5.5 | 22.5 |
| 4 | Etridiazole Fosetyl-Al | WP 30 WP 80 | 2.45 8.71 | 5.8 | 6.5 | 5.5 | 5.5 | 0.5 | 5.5 | 5.8 | 6.0 | 6.0 | 17.3 |
| 5 | Mancozeb | WP 80 | 17.42 | 6.5 | 6.8 | 6.8 | 6.8 | 0.0 | 7.0 | 7.8 | 6.0 | 6.3 | 13.8 |
| 6 | Mancozeb Metalaxyl | WP 80 EC 2 | 17.42 1.36 | 6.5 | 7.0 | 6.8 | 7.0 | 0.0 | 7.0 | 7.8 | 6.0 | 6.8 | 10.0 |
| 7 | Mancozeb Fosetyl-Al | WP 80 WP 80 | 17.42 8.71 | 7.3 | 7.8 | 7.8 | 8.0 | 0.0 | 8.3 | 8.5 | 8.3 | 8.0 | 0.0 |
| 8 | Fosetyl-Al | WP 80 | 8.71 | 6.5 | 6.5 | 6.0 | 6.0 | 0.0 | 5.5 | 5.5 | 6.0 | 6.5 | 21.3 |
| | LSD (0.05) | | | 1.2 | 1.0 | 0.8 | 0.7 | 4.8 | 1.2 | 1.1 | 1.0 | 1.0 | 18.8 |
| | Standard Deviation | | | 0.8 | 0.7 | 0.6 | 0.5 | 3.2 | 0.8 | 0.7 | 0.7 | 0.7 | 12.8 |
| | Coefficient of Variation | | | 12.7 | 10.7 | 9.3 | 7.8 | 280.5 | 13.4 | 11.6 | 11.6 | 11.1 | 67.6 |

| Treatment # | Pesticide Name | Formula | LBai/A | Turf Quality 8/3 | Turf Color 8/3 | Turf Temp. 8/3 | Disease Control 8/10 | Turf Quality 8/12 | Turf Color 8/12 | % Brown Patch 8/12 | Disease Control 8/12 | % Dollar Spot 8/12 |
|---|---|---|---|---|---|---|---|---|---|---|---|---|
| 1 | Check | — | — | 4.0 | 4.5 | 102.8 | 0.0 | 4.0 | 5.0 | 60.0 | 0.0 | 0.0 |
| 2 | Etridiazole | WP 30 | 2.45 | 3.8 | 4.5 | 100.6 | 25.0 | 4.5 | 5.8 | 36.3 | 36.4 | 1.3 |
| 3 | Etridiazole Metalaxyl | WP 30 EC 2 | 2.45 1.36 | 4.3 | 4.8 | 102.8 | 40.6 | 4.8 | 5.5 | 36.3 | 39.0 | 0.0 |
| 4 | Etridiazole Fosetyl-Al | WP 30 WP 80 | 2.45 8.71 | 4.8 | 5.8 | 100.0 | 55.2 | 5.3 | 5.8 | 26.3 | 55.8 | 0.3 |
| 5 | Mancozeb | WP 80 | 17.42 | 5.5 | 6.5 | 100.1 | 61.5 | 5.0 | 5.5 | 50.0 | 16.3 | 0.5 |
| 6 | Mancozeb Metalaxyl | WP 80 EC 2 | 17.42 1.36 | 4.5 | 5.5 | 101.3 | 70.8 | 5.0 | 5.5 | 35.0 | 37.5 | 0.5 |
| 7 | Mancozeb Fosetyl-Al | WP 80 WP 80 | 17.42 8.71 | 8.0 | 8.8 | 98.1 | 100.0 | 7.5 | 8.0 | 7.;5 | 88.8 | 2.3 |
| 8 | Fosetyl-Al | WP 80 | 8.71 | 5.5 | 5.5 | 100.3 | 43.8 | 5.3 | 5.3 | 40.0 | 38.3 | 0.0 |
| | LSD (0.05) | | | 1.4 | 1.2 | 3.6 | 47.8 | 1.3 | 1.1 | 25.8 | 44.8 | 1.9 |
| | Standard Deviation | | | 1.0 | 0.8 | 2.4 | 32.5 | 0.9 | 0.7 | 17.5 | 30.5 | 1.3 |
| | Coefficient of Variation | | | 19.5 | 14.5 | 2.4 | 65.6 | 16.9 | 12.5 | 48.2 | 78.1 | 217.9 |

WP: wettable powder
EC: emulsifiable concentrate
LBai/A: pounds active ingredient per acre As Table 3 indicates, better turf quality and color ratings in the Fosetyl-Al plus Mancozeb treatment indicated a synergistic interaction between these two fungicides at the rates used for the control of the crown and root rot disease. A synergistic interaction was not indicated between the Metalaxyl plus Mancozeb combination since the turf quality and color ratings for this combination were similar to the ratings for Mancozeb alone.

The foregoing examples are illustrative of the present invention, and are not to be construed as limiting thereof. The invention is defined by the following claims, with equivalents of the claims to be included therein.

That which is claimed is:

1. A process for treating bentgrass to enhance turf quality which comprises applying to said bentgrass in an amount effective to enhance turf quality:

(a) one party by weight of a monoester salt of a phosphorous acid of formula (I):

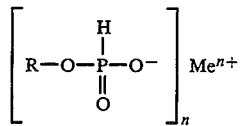

(I)

in which

R is an ethyl radical

Me is an aluminum atom, and n is equal to 3 and (b) from 1.5 to 2.5 part by weight of the contact fungicide manganese-zinc ethylene bisdithiocarbamate.

2. A method according to claim 1, wherein said manganese-zinc ethylene bisdithiocarbamate is applied to said turfgrass in an amount of from 10 to 25 pounds per acre.

3. A method according to claim 1, comprising one part by weight of said monoester salt of a phosphorous acid and two parts by weight of said manganese-zinc ethylene bisdithiocarbamate contact fungicide.

* * * * *